US012318268B2

(12) United States Patent
Cicalis

(10) Patent No.: US 12,318,268 B2
(45) Date of Patent: Jun. 3, 2025

(54) SWAB AND METHOD OF MANUFACTURING A SWAB

(71) Applicant: ARGOS CORPORATION, Taunton, MA (US)

(72) Inventor: Perry Cicalis, East Falmouth, MA (US)

(73) Assignee: Argos Corporation, Taunton, MA (US)

( * ) Notice: Subject to any disclaimer, the term of this patent is extended or adjusted under 35 U.S.C. 154(b) by 388 days.

(21) Appl. No.: 17/228,788

(22) Filed: Apr. 13, 2021

(65) Prior Publication Data

US 2021/0315742 A1    Oct. 14, 2021

Related U.S. Application Data

(60) Provisional application No. 63/008,888, filed on Apr. 13, 2020.

(51) Int. Cl.
*A61F 13/38* (2006.01)
*A61B 10/00* (2006.01)

(52) U.S. Cl.
CPC ........ *A61F 13/385* (2013.01); *A61B 10/0096* (2013.01)

(58) Field of Classification Search
CPC ..... B29C 48/0018; B29C 48/09; A61F 13/38; A61F 13/385
See application file for complete search history.

(56) References Cited

U.S. PATENT DOCUMENTS

| 3,485,234 | A | * | 12/1969 | Stevens | A61M 25/0108 |
| | | | | | 138/123 |
| 3,724,985 | A | * | 4/1973 | Burlis | B29C 48/18 |
| | | | | | 425/380 |
| 3,949,750 | A | * | 4/1976 | Freeman | A61F 9/00772 |
| | | | | | 606/107 |
| 4,135,871 | A | * | 1/1979 | Murai | B29C 48/908 |
| | | | | | 425/467 |
| 4,234,657 | A | * | 11/1980 | Bussey, Jr. | B29C 44/50 |
| | | | | | 428/167 |
| 4,250,072 | A | * | 2/1981 | Flynn | C08K 5/101 |
| | | | | | 524/288 |
| 4,596,563 | A | * | 6/1986 | Pande | A61M 25/0045 |
| | | | | | 604/524 |
| 4,707,450 | A | | 11/1987 | Nason | |
| 4,874,374 | A | * | 10/1989 | Kousai | B29C 48/335 |
| | | | | | 604/528 |

(Continued)

FOREIGN PATENT DOCUMENTS

| CN | 200954009 Y | * | 10/2007 |
| CN | 203252379 U | * | 10/2013 |

(Continued)

OTHER PUBLICATIONS

International Search Report issued in corresponding PCT Application No. PCT/US21/26979 dated Jul. 27, 2021.

*Primary Examiner* — Adam Marcetich
(74) *Attorney, Agent, or Firm* — Grogan, Tuccillo & Vanderleeden, LLP

(57) ABSTRACT

A method of manufacturing a swab for collecting a biological specimen includes extruding a first portion of a stem with at least one of a first taper and/or a first wall thickness, and extruding a second portion of the stem with at least one of a second taper and/or a second wall thickness.

17 Claims, 2 Drawing Sheets

(56) References Cited

U.S. PATENT DOCUMENTS

| | | | | |
|---|---|---|---|---|
| 5,056,841 A * | 10/1991 | Yong | | A47G 21/103 294/23.5 |
| 5,084,005 A * | 1/1992 | Kachigian | | A61B 10/02 600/572 |
| 5,088,991 A * | 2/1992 | Weldon | | A61M 25/0009 604/523 |
| 5,089,204 A * | 2/1992 | Kitao | | B29C 48/903 264/209.4 |
| 5,258,160 A * | 11/1993 | Utsumi | | B29C 48/21 264/40.3 |
| 5,715,559 A * | 2/1998 | Mitri | | A61F 13/38 15/118 |
| 6,595,940 B1 * | 7/2003 | D'Alessio | | A61P 1/02 604/3 |
| 6,641,551 B1 | 11/2003 | Prager | | |
| 6,795,998 B1 * | 9/2004 | Kammerer | | B08B 1/00 15/159.1 |
| 2002/0022101 A1 * | 2/2002 | Lenthe | | B29C 55/26 428/36.9 |
| 2003/0199836 A1 * | 10/2003 | Tiernan | | B29C 48/21 264/209.4 |
| 2003/0204169 A1 * | 10/2003 | Howell | | B29C 48/13 264/209.3 |
| 2004/0158188 A1 * | 8/2004 | Kauffmann | | A61B 10/0096 604/1 |
| 2004/0197730 A1 * | 10/2004 | Rowe | | A61C 5/60 433/80 |
| 2005/0008806 A1 * | 1/2005 | Schewe | | B29C 48/10 428/36.9 |
| 2005/0040164 A1 * | 2/2005 | Tsaur | | B65D 67/02 220/4.26 |
| 2005/0076461 A1 * | 4/2005 | Tsaur | | A61F 13/38 15/209.1 |
| 2005/0080507 A1 * | 4/2005 | Silberg | | B29C 48/92 700/196 |
| 2005/0116482 A1 * | 6/2005 | Harris | | A47G 21/103 294/218 |
| 2006/0084032 A1 * | 4/2006 | Tipton | | A61C 3/00 433/141 |
| 2006/0228159 A1 * | 10/2006 | Phillips | | A61C 3/00 401/126 |
| 2007/0134367 A1 * | 6/2007 | Zoppas | | B29C 45/27 425/549 |
| 2008/0027367 A1 * | 1/2008 | Abarbanel | | A61M 35/006 604/1 |
| 2008/0119776 A1 | 5/2008 | Wu | | |
| 2009/0110761 A1 * | 4/2009 | Kikusawa | | B29C 48/501 425/131.1 |
| 2009/0126204 A1 * | 5/2009 | Wagner | | B65D 65/466 206/524.6 |
| 2009/0216172 A1 * | 8/2009 | Houtan | | A61F 13/38 422/40 |
| 2009/0227962 A1 * | 9/2009 | Eversull | | B29C 66/83413 156/196 |
| 2011/0106121 A1 * | 5/2011 | Zaldivar | | A61F 13/36 606/162 |
| 2012/0121482 A1 * | 5/2012 | Ochman | | B29C 67/0014 422/524 |
| 2013/0122293 A1 * | 5/2013 | Weber | | B29C 48/154 264/103 |
| 2014/0083213 A1 * | 3/2014 | Triva | | A61B 10/02 73/864 |
| 2014/0106298 A1 * | 4/2014 | Kassab | | A46B 11/001 433/226 |
| 2014/0289986 A1 * | 10/2014 | Hani | | A61F 13/38 106/160.1 |
| 2015/0291779 A1 | 10/2015 | Hani et al. | | |
| 2016/0367227 A1 * | 12/2016 | Triva | | C12M 33/02 |
| 2017/0065261 A1 * | 3/2017 | Ching | | A61B 10/02 |
| 2017/0135782 A1 * | 5/2017 | Kassab | | A61C 5/62 |
| 2017/0196386 A1 * | 7/2017 | Tran | | A47G 21/103 |
| 2017/0196387 A1 * | 7/2017 | Tran | | A47G 21/103 |
| 2018/0030396 A1 * | 2/2018 | Peltosaari | | B01L 3/18 |
| 2018/0036725 A1 * | 2/2018 | Le | | B29C 49/50 |
| 2018/0161019 A1 * | 6/2018 | Donovan | | B01L 3/5029 |
| 2018/0361375 A1 * | 12/2018 | Martello | | B01L 3/5055 |
| 2020/0140631 A1 * | 5/2020 | Sorenson | | C08K 5/34924 |
| 2020/0157832 A1 * | 5/2020 | Van Hoek-Patterson | | E04B 1/944 |
| 2020/0164564 A1 * | 5/2020 | Cadotte, Jr. | | B29C 49/36 |

FOREIGN PATENT DOCUMENTS

| | | | | |
|---|---|---|---|---|
| CN | 106235839 A | * | 12/2016 | |
| CN | 106618089 A | * | 5/2017 | |
| CN | 108577436 A | * | 9/2018 | ........... A47G 21/103 |
| EP | 2745818 A1 | * | 6/2014 | ............. A61F 13/36 |
| KR | 20110006452 U | * | 6/2011 | |
| WO | WO-2005104920 A1 | * | 11/2005 | ........... A47G 21/103 |
| WO | WO-2007070415 A2 | * | 6/2007 | ............. A47G 19/00 |

* cited by examiner

SWAB AND METHOD OF MANUFACTURING A SWAB

CROSS-REFERENCE TO RELATED APPLICATIONS

This application claims the benefit of U.S. Provisional Application Ser. No. 63/008,888, filed on Apr. 13, 2020, which is hereby incorporated by reference herein in its entirety.

FIELD OF THE INVENTION

The present invention relates generally to swabs for collecting biological specimens and, more particularly, to a tapered swab and method of manufacturing a tapered swab.

BACKGROUND OF THE INVENTION

Swabs for use in the collection of biological specimens of organic material for clinical and diagnostic analysis have been known in the art for quite some time. Known swabs typically consist of a cylindrical rod or stem, the distal tip of which carries an absorbent material with hydrophilic properties to allow rapid absorption of the quantity of specimen to be collected and tested. For example, the absorbent material may be a wad of fiber such as rayon, or a natural fiber such as cotton. Stable adherence of the fiber wrapped around the tip of the rod is generally achieved by gluing. Other swabs have fibers disposed on the distal tip by flocking in an electrostatic field.

Recent advancements in the field of biological specimen collection have led to the development of swabs having two different stages or portions, for example, a first stem portion having a first diameter, and a second stem portion having a second, and perhaps smaller, diameter. The first stem portion provides stiffness, allowing the swab to be handled and manipulated easily, while the second stem portion imparts flexibility, allowing the swab to more easily conform or adapt to narrow passages within the body such as, for example, when collecting a specimen from the posterior nasopharynx.

Such existing swabs are typically manufactured by injection molding techniques. Injection molding, however, can leave a parting line along the length of the swab where the two mold halves come together and separate, which can scratch or irritate sensitive tissues during specimen collection. Moreover, injection molding requires expensive molds that are not easily configurable. Accordingly, the swab configurations that can be produced using a given mold are quite limited.

In view of the above, there is a need for an improved swab and method of manufacturing a swab that overcomes the limitations of existing swabs and, in particular, injection molded swabs.

SUMMARY OF THE INVENTION

It is an object of the present invention to provide a swab.
It is another object of the present invention to provide a swab for collecting a biological specimen.
It is another object of the present invention to provide a swab having a tapered stem.
It is another object of the present invention to provide a swab having two or more sections having different mechanical and/or functional properties or characteristics.

It is another object of the present invention to provide a swab having a stiff section and a flexible section.
It is yet another embodiment of the present invention to provide a swab having a stem that allows for the attachment of various styles of collection swabs at a distal tip thereof.
It is yet another object of the present invention to provide a method of manufacturing a swab.
It is yet another object of the present invention to provide a method of manufacturing a swab that allows for easy customization of rod strength and/or flexibility.
It is yet another object of the present invention to provide a method of manufacturing a swab that allows the taper of the rod to be easily varied.

These and other objects are achieved by the present invention.

According to one embodiment of the present invention, a method of manufacturing a swab for collecting a biological specimen includes extruding a first portion of a stem with at least one of a first taper and/or a first wall thickness, and extruding a second portion of the stem with at least one of a second taper and/or a second wall thickness.

According to another embodiment of the present invention, a swab for collecting a biological specimen includes a stem having a proximal end and a distal end, and an absorbent material connected to the distal end for collecting the biological specimen. The stem includes a tapered section between the proximal end and the distal end.

According to yet another embodiment of the present invention, a method of manufacturing a swab for collecting a biological specimen includes extruding a first portion of a stem having a first taper, and extruding a second portion of the stem integral with the first portion, the second portion having one of a constant outside diameter or a second taper.

BRIEF DESCRIPTION OF THE DRAWINGS

The present invention will be better understood from reading the following description of non-limiting embodiments, with reference to the attached drawings, wherein below.

DETAILED DESCRIPTION OF THE PREFERRED EMBODIMENT

Figure 1:
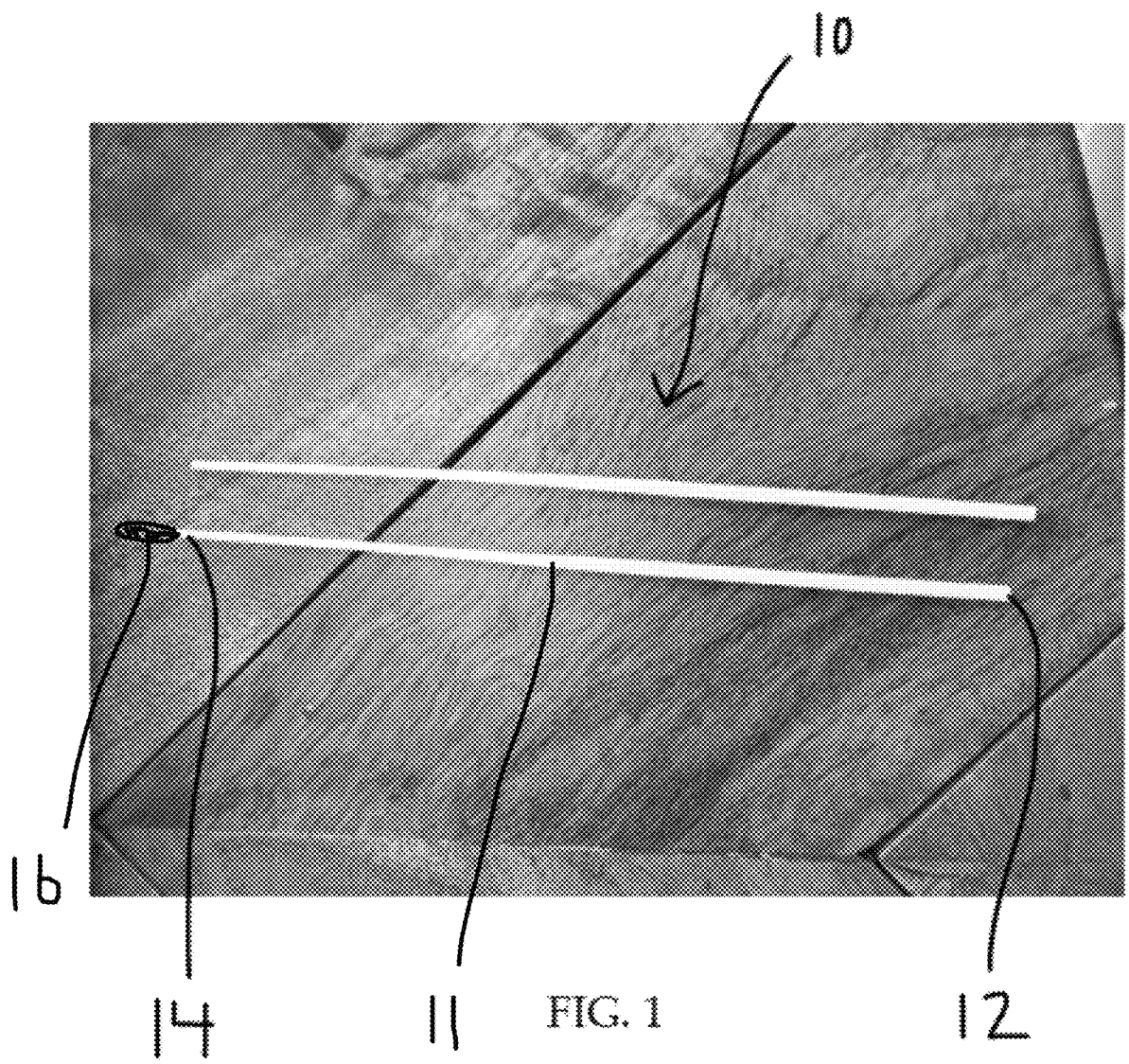
FIG. 1 is a perspective view of a pair of stems of a swab according to an embodiment of the present invention.

Referring to FIG. 1, a swab 10 having a stem 11 according to one embodiment of the present invention is illustrated. The stem 11 includes a proximal end 12 and a distal end or tip 14. In an embodiment, the stem 11 is tapered, having a larger diameter or cross-sectional area adjacent to the proximal end 12, which decreases progressively moving towards the distal end 14. Importantly, the tapered configuration of the stem 11 provides greater strength and rigidity adjacent to the proximal end 12, and greater flexibility moving towards the distal end 14, which is advantageous when used for collecting a biological specimen, as discussed hereinafter.

In an embodiment, as shown in FIG. 1, the stem 11 may be tapered along its entire length, namely, the stem 11 may have a continuous taper from the proximal end to the distal end 14. In an embodiment, the angle of the taper may vary. In yet other embodiments, it the stem may be cylindrical along a first portion of its length, and tapered along a second portion of its length. More than two stem segments of different configuration (i.e. cylindrical versus tapered, angle of taper, etc.) may be employed to achieve functional or performance characteristics desired. In an embodiment, the stem may be solid. In other embodiments, the stem may be hollow or have a lumen.

In an embodiment, the stem 11 of the swab is formed or manufactured via extrusion. For example, in an embodiment, the stem 11 is extruded by first adding specific raw material, such as a polymer, into a hopper located above the screw opening at the rear of the extruder. The screw, and barrel that contains the screw, are heated, and melt the polymer in a gradual staging process, as the screw moves the material forward toward the front of the extruder. At the front of the extruder, the melted polymer is forced through a die that determines the shape of the part to be produced, e.g., a rod, or a tube. Once it exits the face of the extrusion machine, the melted material (i.e. extrudate) may be guided into a tool designed to set the material up into the shape of the finished product (in this case, a swab). In particular, the extrudate is cooled and shaped into its final configuration or form using air pressure, a cooling tank and/or sizing tooling.

To form a hollow stem (i.e., with an interior lumen), during the extrusion process, air at a specific pressure is used to obtain the intended tubing shape. In particular, low air pressure is injected into the die, which flows through the center of the pin that makes up the inner part of the extrusion die, and then directly into the semi-fluid tubing as it is coming out of the die. Sizeable diameter variations can be caused by the slightest pressure change during the extrusion of thin-walled products. By controlling the extrusion rate, along with the internal air pressure of the tubing, desired values for the outside diameter and wall thickness can be achieved.

At the end of the extrusion line, a takeoff unit or puller pulls tension on the extrudate as it exits the extruder, and essentially is what controls the line speed and to some degree, the part size, as it pulls tension on the extrudate and maintains stability during the course of the run. As discussed hereinafter, to vary/control the taper length, position and diameter of the extruded stem 11, the haul-off speed is varied/controlled. This is done in conjunction with air pressure to create the desired diameter and wall thickness of the stem 11, as alluded to above.

By utilizing extrusion to form the stem 11, parting lines (which are common on injection molded parts) are eliminated, resulting in a swab 10 that is much less likely to scratch or irritate tissues. In addition, extrusion allows for much more flexibility and customization of the configuration of the stem 11. In particular, the stem 11 may be formed with a plurality of integral portions or sections having different mechanical or functional characteristics simply by changing the speed of the takeoff unit (for both solid and hollow stems) and/or by changing the air pressure within the lumen of the part during the extrusion process (for hollow stems).

For example, the speed of the takeoff unit and/or air pressure may be varied during the extrusion process in order to impart various mechanical and/or functional characteristics to different longitudinal sections of the stem 11. In particular, changing the speed of the takeoff unit can be used to create the taper (and degree/angle of taper) in the stem 11. For example, the takeoff unit and servomotors thereof, are operated under control of a controller so that off speed can be varied to create the taper in the extruded stem. Slowing the takeoff speed increases the diameter of the stem and taper, increasing the takeoff speed causes the stem to taper down to a smaller diameter. Similarly, for hollow stems, changing the air pressure can be used to selectively increase or decrease the diameter or wall thickness of the stem 11.

Forming the stem 11 via extrusion therefore allows taper length to be easily adjusted to provide for more comfort and functionality. As alluded to above, the stem 11 may be formed with a plurality of integral sections having different taper configurations and/or wall thicknesses (e.g., a first tapered section, having a taper of a first angle, and a second tapered section having a taper of a second angle, where the second angle is different from the first angle). In an embodiment, the stem 11 may have three or more integral sections with different taper configurations and/or wall thicknesses.

In connection with the above, the lengths of the various sections may be selected in dependence upon the specific anatomy of a subject. For example, the stem may have a first section of relatively large diameter or wall thickness designed to impart strength and rigidity to the proximal end of the stem, and a second section of reduced diameter or wall thickness designed to allow for flexing of the stem throughout the longitudinal extent of the second section. Moreover, the length of the second section may be chosen so as to correspond to the length of a passage within which the swab is intended to be inserted for specimen collection, e.g., the length of the nasal or nasopharyngeal passage. In certain embodiments, the stem 11 may be manufactured with a hollow distal end portion, and a solid proximal end portion, and vice versa.

As illustrated in FIG. 1. It is contemplated that the distal tip 14 of the stem 11 may be outfitted with an absorbent material 16 particularly suited for biological specimen collection. For example, it is contemplated that the absorbent material (e.g., fibers) may be disposed on the distal end 14 of the stem 11 such as by flocking or gluing. In addition, it is contemplated that a swab head may be coupled to the distal end 14 of the stem 11 via insertion into the inside diameter of the stem (for hollow stems) or by bonding to the outside diameter of the stem 11. Further, it is envisioned that the swab head may be a twisted wire head having fibers anchored therein or coupled thereto by flocking or other techniques.

Figure 2:
FIG. 2 is a perspective view of a prior art swab.

Whereas the flexibility and stiffness of existing injection molded swabs are typically limited by the use of a single material due to the longitudinal nature of the stem, the extruded swabs of the present invention provide for an almost unlimited array of stem configurations and variations in the functional properties thereof, by selectively controlling the taper, wall thickness, and/or solid or hollow cross-section at various points along the stem. FIG. 2 illustrates a prior art, injection molded swab having two different sections. As will be appreciated, however, such prior art swabs have heretofore been formed with only two different sections, and customization is not possible in most cases without production of a new mold or significant alteration of existing molds.

As indicated above, the method of the present invention allows for mechanical and functional properties of the stem (and swab) to be varied by using the taper to adjust for strength or flexibility. For instance, a high strength material suitable for a specific property such as a chemical reagent resistance can be tapered to a smaller diameter or thinner wall to accommodate specific uses. Moreover, it is contemplated that a tube or shape can be coextruded or braided to adjust for being pushed around contours of the nasal passage.

As indicated above, the taper of the stem 11 may be in multiples (e.g., two or three or more different tapers) along length to allow for more flexibility in design of swab or brush. In other words, the stem 11 may have a wave of various inside diameter, outside diameter, and wall combinations.

As will be appreciated, extrusion is advantage over injection molding in terms of cost, and allows for the scaling of product without needing a secondary process for stretching thin areas. In addition, scoring can be done inline while extruding to notch (e.g., notching is not an issue with extrusion). For example, a score or notch can be added inline or offline and can be 360 degrees around the circumference or one sided. This will be dependent on material notch sensitivity and product need, e.g., collection of a portion of the swab into a test tube. Moreover, the handle (proximal) and functional (distal) end of the step can be varied without the cost associated with building a mold (which may be hundreds of thousands of dollars), as tool change in extrusion is much lower cost.

In yet another embodiment of the present invention, it is envisioned that coextrusion can be utilized to impart properties of two or more materials to the stem, e.g., hard and soft inner or outer, lubricious outer, etc. In an embodiment, dual durometer material may be utilized to form the stem to provide the same functional benefits achieved using a tapered stem or variation in wall thickness as discussed above. For example, a first, stiff or rigid material may be used to form the proximal end of the stem, and a second, flexible material may be used to form the distal end of the stem. The stem may be formed with different materials as part of an in-line extrusion process.

While the stem 11 has been disclosed as being formed using extrusion, the present invention is not so limited in this regard. In particular, it is contemplated that the tapered configuration of the stem 11 may be formed using injection molding (with a tapered mold) or other techniques, the important aspect being the ability to form a taper along the stem 11 so as to provide strength and stiffness adjacent to the proximal end where it will be grasped by a user, and flexibility towards the distal end to provide smooth and easy insertion into narrow passages.

Finally, while the stem has been disclosed herein as forming a part of biological specimen collection swab, the present invention is not so limited in this regard. In particular, it is envisioned that the teachings herein may be utilized to impart varying mechanical and/or functional characteristics to stems and structures intended for various end uses where a combination of strength/rigidity and flexibility may be desired.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A method of manufacturing a swab for collecting a biological specimen, comprising the steps of:
   extruding a first portion of a stem having a first taper that is continuous and uniform from one end of the first portion of the stem to an opposing end; and
   extruding a second portion of the stem integral with the first portion, the second portion having one of a constant outside diameter or a second taper that is continuous and uniform from one end of the second portion of the stem to an opposing end;
   wherein the first portion and the second portion are directly adjacent to one another;
   wherein the first portion of the stem is solid and devoid of an interior passage; and
   wherein the second portion is cylindrical in shape and has a constant outside diameter.

2. The method according to claim 1, further comprising the step of:
   varying a take-off speed of an extrusion system to control an angle of the first taper or the second taper.

3. The method according to claim 1, wherein:
   the first taper of the first portion of the stem is devoid of any steps.

4. A method of manufacturing a swab for collecting a biological specimen, comprising the steps of:
   extruding a first portion of a stem having a first taper that is continuous and uniform from one end of the first portion of the stem to an opposing end;
   extruding a second portion of the stem integral with the first portion, the second portion having one of a constant outside diameter or a second taper that is continuous and uniform from one end of the second portion of the stem to an opposing end; and
   securing an absorbent material to a distal end of the stem;
   wherein the first portion and the second portion are directly adjacent to one another; and
   wherein the first portion of the stem is solid and devoid of an interior passage.

5. The method according claim 4, wherein:
   the second portion includes the second taper.

6. The method according to claim 5, wherein:
   a degree of the first taper and the second taper is the same.

7. The method according to claim 5, wherein:
   a degree of the first taper and the second taper, respectively, is different.

8. A method of manufacturing a swab for collecting a biological specimen, comprising the steps of:
   extruding a first portion of a stem with a first wall thickness, the first portion of the stem having a first taper that is continuous and uniform from one end of the first portion to an opposing end;
   extruding a second portion of the stem with a second wall thickness that is integral with the first portion such that a parting line between the second portion and the first portion is eliminated, the second portion of the stem having a second taper that is continuous and uniform from one end of the second portion to an opposing end;
   wherein the first section is formed from a first material and the second section is formed from a second material that is different from the first material,
   wherein the stem formed from the first portion and the second portion comprises a proximal end adjacent the first portion and a distal end adjacent the second portion, and
   wherein the stem comprises a taper that is continuous and uniform from the proximal end to the distal end, the taper decreasing in a substantially straight path along an entire length of the stem covering the first portion and the second portion from the proximal end to the distal end.

9. The method according to claim 8, further comprising the step of:

extruding a third portion of the stem with a third wall thickness that is integral with the first portion and the second portion, the third portion of the stem having a third taper, wherein the third portion of the stem is disposed between the first portion and the second portion.

10. The method according to claim 8, wherein:

at least one of the first portion and the second portion of the stem is hollow.

11. The method according to claim 8, wherein:

the first taper of the first portion has an angle that increases moving from a proximal end of the first portion to a distal end of the first portion.

12. A method of manufacturing a swab for collecting a biological specimen, comprising the steps of:

extruding a first portion of a stem having a first taper that is continuous and uniform from one end of the first portion of the stem to an opposing end; and extruding a second portion of the stem integral with the first portion, the second portion having one of a constant outside diameter or a second taper that is continuous and uniform from one end of the second portion of the stem to an opposing end;

wherein the first portion and the second portion are directly adjacent to one another;

wherein the first portion of the stem is solid and devoid of an interior passage; and wherein at least one of the first portion and the second portion is formed via coextrusion such that an inner layer has a property that is different from a property of an outer layer.

13. A method of manufacturing a swab for collecting a biological specimen, comprising the steps of:

extruding a first portion of a stem having a first taper that is continuous and uniform from one end of the first portion of the stem to an opposing end; and extruding a second portion of the stem integral with the first portion, the second portion having one of a constant outside diameter or a second taper that is continuous and uniform from one end of the second portion of the stem to an opposing end;

wherein the first portion and the second portion are directly adjacent to one another;

wherein the first portion of the stem is solid and devoid of an interior passage; and wherein the stem has a hollow distal end and a solid proximal end.

14. A method of manufacturing a swab for collecting a biological specimen, comprising the steps of:

extruding a first portion of a stem having a first taper that is continuous and uniform from one end of the first portion of the stem to an opposing end; and extruding a second portion of the stem integral with the first portion, the second portion having one of a constant outside diameter or a second taper that is continuous and uniform from one end of the second portion of the stem to an opposing end;

wherein the first portion and the second portion are directly adjacent to one another;

wherein the first portion of the stem is solid and devoid of an interior passage; and wherein the first section is formed from a first material and the second section is formed from a second material that is different from the first material.

15. A method of manufacturing a swab for collecting a biological specimen, comprising the steps of:

extruding a first portion of a stem having a first taper that is continuous and uniform from one end of the first portion of the stem to an opposing end; and extruding a second portion of the stem integral with the first portion, the second portion having one of a constant outside diameter or a second taper that is continuous and uniform from one end of the second portion of the stem to an opposing end;

wherein the first portion and the second portion are directly adjacent to one another;

wherein the first portion of the stem is solid and devoid of an interior passage; and wherein a length of the first portion corresponds to a length of a pharyngeal passage of a human.

16. A method of manufacturing a swab for collecting a biological specimen, comprising the steps of:

extruding a first portion of a stem having a first taper that is continuous and uniform from one end of the first portion of the stem to an opposing end; and extruding a second portion of the stem integral with the first portion, the second portion having one of a constant outside diameter or a second taper that is continuous and uniform from one end of the second portion of the stem to an opposing end;

wherein the first portion and the second portion are directly adjacent to one another;

wherein the first portion of the stem is solid and devoid of an interior passage; and wherein the extruding of the first portion and the second portion of the stem imparts the first portion with a flexibility that allows for flexing of the stem throughout a longitudinal extent of the first portion that is elastic without plastic deformation, and imparts the second portion about the proximal end of the stem to have more strength and rigidity in relation to the first portion about a distal end of the stem.

17. A method of manufacturing a swab for collecting a biological specimen, comprising the steps of:

extruding a first portion of a stem having a first taper that is continuous and uniform from one end of the first portion of the stem to an opposing end;

extruding a second portion of the stem integral with the first portion, the second portion having one of a constant outside diameter or a second taper that is continuous and uniform from one end of the second portion of the stem to an opposing end; and securing a plurality of fibers to a distal end of the first portion of the stem.

* * * * *